United States Patent [19]

Kaiser

[11] Patent Number: 4,524,234

[45] Date of Patent: Jun. 18, 1985

[54] PRODUCTION OF HYDROCARBONS WITH ALUMINOPHOSPHATE MOLECULAR SIEVES

[75] Inventor: Steven W. Kaiser, South Charleston, W. Va.

[73] Assignee: Union Carbide Corporation, Danbury, Conn.

[21] Appl. No.: 663,080

[22] Filed: Oct. 19, 1984

[51] Int. Cl.³ ............................................... C07C 1/00
[52] U.S. Cl. ................................... 585/638; 585/639; 585/640; 585/642; 585/469; 585/733; 208/262; 208/213; 208/254 R
[58] Field of Search .............. 585/638, 639, 642, 469, 585/733, 640

[56] References Cited

U.S. PATENT DOCUMENTS

| | | | |
|---|---|---|---|
| 3,894,105 | 7/1975 | Chang et al. | 260/668 |
| 3,894,106 | 7/1975 | Chang et al. | 260/668 |
| 3,894,107 | 7/1975 | Butter et al. | 260/668 |
| 3,965,205 | 6/1976 | Garwood et al. | 260/668 |
| 3,998,898 | 12/1976 | Chang et al. | 260/668 |
| 4,062,905 | 12/1977 | Chang et al. | 260/668 |
| 4,079,095 | 3/1978 | Givens et al. | 260/682 |
| 4,079,096 | 3/1978 | Givens et al. | 260/682 |
| 4,310,440 | 1/1982 | Wilson et al. | 252/435 |

FOREIGN PATENT DOCUMENTS

| | | | |
|---|---|---|---|
| 317500 | 8/1929 | United Kingdom | 585/639 |
| 589709 | 7/1942 | United Kingdom | 585/639 |

Primary Examiner—D. E. Gantz
Assistant Examiner—Cynthia A. Prezlock
Attorney, Agent, or Firm—Gary L. Wamer

[57] ABSTRACT

The process for the production of hydrocarbons from a feedstock comprising compounds of the formula R—X wherein X is a moiety containing at least one of halogen, sulfur, oxygen, and nitrogen, wherein the feedstock is contacted with an aluminophosphate molecular sieve of U.S. Pat. No. 4,310,440 at effective process conditions to produce light olefin products.

32 Claims, No Drawings

PRODUCTION OF HYDROCARBONS WITH ALUMINOPHOSPHATE MOLECULAR SIEVES

FIELD OF THE INVENTION

The present invention relates to a new catalytic process for the production of hydrocarbons, particularly, light olefins, i.e., olefins having not more than four carbon atoms, from a feedstock comprising alcohols, mercaptans, ethers, sulfides, amines, carbonyl compounds and mixtures thereof in the presence of an aluminophosphate molecular sieve catalyst.

BACKGROUND OF THE INVENTION

As a result of the limited availability and high cost of petroleum sources the cost of producing chemicals from such petroleum sources has been steadily increasing. Further, many in the chemical industry, as well as elsewhere, have predicted significant oil shortages in the not too distant future. As a result, there has been a search for alternative, low cost and more readily available raw materials for chemical synthesis with the ultimate goal being the derivation of valuable chemical products from non-petroleum sources.

Examples of readily available non-petroleum sources are methanol, ethanol and their derivatives which may be manufactured from non-petroleum sources, such as by fermentation or from synthesis gas, i.e. a mixture of hydrogen and oxides of carbon. Synthesis gas may be derived by the combustion of any carbonaceous material including coal, or any organic material, such as hydrocarbons, carbohydrates and the like. Thus, the use of methanol and its derivatives to form chemical products is particularly desirable in providing such a non-petroleum based route. The manufacture of methanol from synthesis gas by a heterogeneous catalytic reaction is presently an efficient commercial process.

Although methanol and its derivatives have for some time been considered as desirable starting materials for the manufacture of chemicals (which it is, e.g., in the manufacture of formaldehyde), the use of such as a replacement for petroleum or natural gas in commercial chemical syntheses has not been vast. If processes can be developed for the use of methanol and its derivatives for the commercial manufacture in large volume of chemical products or intermediates then the present dependence on petroleum sources as the basic raw material for chemical synthesis may be substantially lessened.

One proposed way to use methanol and its derivatives to manufacture chemical products is by catalytically converting them with crystalline aluminosilicate zeolites. Representative of the various contemplated processes using such crystalline aluminosilicate zeolites, and as more completely discussed hereinafter, are those processes disclosed in U.S. Pat. Nos.: 3,894,107; 4,046,825; 4,062,905; 4,079,095; 4,079,096; 3,911,041; and 4,049,573. What appears to be evident from the above patents, as well as other patents, is that the process is tied to the particular catalyst employed yielding differences in: product ratios (as well as by-product formation); catalyst life; conversion to product; selectivity to product; catalyst attrition; and the effects from additives to the catalytic process. The significance of these differences is readily apparent by reviewing the divergent results of the published art wherein various catalysts have been employed for the conversion of methanol to light olefin products. Representative of this art are: European Application No. 6,501 (catalyst is HZSM-5); European Application No. 2,492 (catalyst is Mn exchanged 13X zeolite); German Offen. 2,909,928 (catalyst is Fe exchanged Silicalite); Agnew. Chem. Int. Ed., 19, 2 (1980), 126-127 (catalyst is Mn exchanged Chabazite and erionite); South African 78/2527 (catalyst is CaH-Fu-1 zeolite); and European Application 11,900 (catalyst is boron modified silica).

For example, German Offen. 2,909,928 discloses a 95-100 percent conversion with 5.2 weight percent of the product as ethylene, whereas the publication Agnew. Chem. Int. Ed., 19, 2 (1980), 126-7 discloses a conversion of about 82 percent with 35.7 weight percent of the product as ethylene.

A brief discussion of selected patents and publications will further serve to point out differences involved in the conversion of methanol and derivatives thereof to light olefin products.

U.S. Pat. No. 4,062,905 discloses a process for the conversion of methanol, dimethyl ether or mixtures thereof to hydrocarbon products rich in ethylene and propylene using a catalyst comprising a crystalline aluminosilicate zeolite characterized by pores, the major dimension of which, are less than 6 Angstroms, the pores being further characterized by pore windows of about a size as would be provided by 8-membered rings of oxygen atoms. The process is alleged to have the capability under certain conditions of producing less than 20 weight percent methane by weight of the hydrocarbon product. The claimed correlation in the patent between pore size, process conditions and the level of methane production is admittedly specifically limited to the crystalline aluminosilicate zeolites, see the quote below.

The passage beginning at column 3, line 5 (also see Example 17) of U.S. Pat. No. 4,062,905 demonstrates this view:

"In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5A, while satisfying the pore size requirements for zeolites useful as catalysts in the process described herein, is nevertheless, not a particularly feasible catalyst since under the conversion conditions utilized in such process, this zeolite produces considerable amounts of methane, i.e. far in excess of the specified maximum of 20 weight percent characterizing the crystalline aluminosilicate zeolites which have been found to be effective in selectively converting methanol and/or dimethyl ether to ethylene and propylene".

Even when a crystalline aluminosilicate zeolite having the desired physical and chemical properties is employed it may not be useful as a catalyst according to the patent's process. Thus, this patent discloses that the chemical composition of an aluminosilicate which has a desirable pore size may or may not be determinative as to whether it will produce methane at a given rate such that less than 20 percent by weight methane is produced.

The specificity of the catalysts in this field is demonstrated by U.S. Pat. Nos. 4,079,096 and 4,079,095 which disclose processes for the conversion of methanol, dimethyl ether or mixtures thereof to hydrocarbon products, such as ethylene and propylene, by contacting them with a catalyst comprising, respectively, a crystalline aluminosilicate zeolite of the erionite-offretite family and, the particular erionite-offretite of the crystalline aluminosilicate zeolite ZSM-34. The processes are limited to the use of crystalline aluminosilicates having substantially the same diffraction pattern as the erionite-offretite family.

U.S Pat. No. 3,911,041 describes the conversion of methanol or dimethyl ether by contacting them with a crystalline aluminosilicate zeolite having a silica to alumina ratio of at least about 12, a constraint index of about 1 to 12, and containing phosphorous deposited on the crystal structure thereof in an amount of at least about 0.78 percent by weight. The phosphorous is disclosed as not in the framework of the crystalline aluminosilicate, as can be determined from the preparation procedure beginning at column 7, line 56 of the patent. The procedure set forth in the patent details that the crystalline aluminosilicate zeolite is formed prior to the addition of the phosphorus-containing compound, after which the phosphorous-containing compound is "reacted" with the surface sites of the zeolite to provide a surface treated material. Further, X-ray diffraction analyses of the zeolite before and after treatment with a phosphorus-containing compound showed substantially identical interplanar spacings (see Column 8, lines 54 to 64) indicating that no phosphorus was present in the framework. The surface treatment of the crystalline aluminosilicates is predicated on the patentees' belief that the number and strength of the aluminosilicates acid sites is related to the activity.

U.S. Pat. No. 4,049,573 describes a crystalline aluminosilicate zeolite having a silica to alumina ratio of at least 12 and a constraint index within the approximate range of 1 to 12, and having deposited thereon (as one of several possibilities) between about 0.25 and about 10 percent by weight of phosphorus oxide in combination with between about 0.25 and about 5 percent by weight of boron oxide and between about 2 and about 15 percent by weight of magnesium oxide. As was the case in the above-discussed U.S. Pat. No. 3,911,041, the phosphorous oxide, boron oxide and magnesium oxide are not incorporated into the zeolite framework but, instead, are added to the zeolite after the framework of the aluminosilicate zeolite has been formed, i.e. are provided as a post treatment of the aluminosilicate zeolite, apparently for the same reason.

As is evident from the above, the interest in selective catalysts for the manufacture of light olefins from methanol has been achieved from a special aluminosilicate structure or by achieving modifications of aluminosilicates by deposition with special additives. As above-noted, one of these was to deposit a phosphorous-containing compound (termed "doping" therein) in combination with a number of other compounds on an aluminosilicate zeolite.

U.S. Pat. Nos. 3,911,041 and 4,049,573, reports the sorption of phosphate ions onto amorphous metal oxides and combinations of metal oxides. Such sorptions of phosphate ions has been intensively studied in such areas as in the chemistry of soil, although such studies have not heretofore reported a crystalline microporous phosphate-containing material. For example, see: S. S. Rajan and K. W. Perrott, J. Soil Sci., 26, 257 (19751); J. A. Veith and G. Sposito, Soil. Sci., Soc. Am. J., 41, 870 (1977); E. A. Ferreiro and S. G. DeBussetto, Agrochimica, 24,184 (1980).

It has been reported (D. McConnell, Ameri. Min., 37, 609 (1952)) that certain natural aluminosilicate zeolites may have $PO_2^+$ substitution into the tetrahedral framework with such a substitution being reported in viseite which is considered to be isostructural with analcime. D. McConnell reported an elemental composition of:

$$5CaO:5Al_2O_3:3SiO_2:3P_2O_5:nH_2O.$$

This report should be viewed cautiously, if not with skepticism, in view of the considerable question of agreement on the X-ray powder diffraction patterns of such a substituted viseite and analcime owing to the highly defective structure (with dangling—OH groups wherever tetrahedral cation vacancies occur) resorted to in order to substantiate such structures as being isostructural.

R. M. Barrer and D. J. Marshall (J. Chem. Soc., 1965, 6616 and 6621) reported the attempted substitution of phosphorus in aluminosilicates during hydrothermal crystallizations in the system, in respect to the following:

$$Al_2O_3—SiO_2—P_2O_5—base—H_2O$$

Although phosphate was observed to co-precipitate with the aluminosilicates in this system there was no evidence that an aluminosilicophosphate framework had formed.

R. M. Barrer and M. Liquornick (J. Chem. Soc., Dalton Trans., 2126 (1974)) reported that by use of metakaolinite and phosphoric acid, and in some instances by further addition of silica, that zeolites were formed having an extremely low content of phosphorous with a maximum of 0.0117 atoms of phosphorus present per atom of aluminium. The authors explanation for this very low phosphorous content is that phosphate anions were trapped in cavities within the zeolite framework rather than actually being in the framework.

U.S Pat. No. 3,443,892 discloses a process for making Zeolite X by mixing aluminum phosphate with hot sodium silicate to give an as-synthesized product having the general formula:

(0.5–1.1) $Na_2O_3:Al_2O_3:(0–0.2)P_2O_5$: (2.3–3.3)$SiO_2$:(0–7.2)$H_2O$

No chemical data is disclosed by the patentee for determining the framework structure and the patent requires that the ratio of $SiO_2$ to $Na_2O$ in the reaction mixture must be less than 1.

The synthesis of aluminosilicophosphate zeolite analogues having phosphorus incorporated into the tetrahedral sites of the zeolite-type framework during hydrothermal synthesis employing substantial amounts of alkali metal cations has been reported by E. M. Flanigen and R. W. Grose at Advances in Chem., Series No. 101 pages 76–101 (1971). (Also see: Canadian Pat. No. 911,410, issued Oct. 3, 1972 to Robert W. Grose and Edith M. Flanigen) In this report the authors reported compositions with the following types of zeolite-type frameworks: analcime, chabazite, phillipsite-harmotome, Type A zeolite, Type L zeolite, and Type B (P) zeolite. These compositions were reported to contain between 5 and 25 percent by weight $P_2O_5$ incorporated into the zeolite-type frameworks. The substitution of phosphorus for silicon did not appear to impart beneficial properties to the compositions not possessed by analogous aluminosilicate compositions, although differences were reported in some of the compositions, e.g. reduced adsorption capacity and reduced thermal stability on thermal activation. Many of the physical and chemical properties of the phosphorus-substituted analogues were inferior to those of the unsubstituted species.

A new class of silicoaluminophosphates is disclosed in U.S. Pat. No. 4,440,811. The use of such silicoaluminophosphates for the conversion of methanol to light olefins is disclosed in copending and commonly assigned U.S. Ser. No. 426,213, filed Oct. 4, 1982.

SUMMARY OF THE INVENTION

This invention comprises a process for the catalytic conversion of a feedstock comprising an organic compound having the formula R—X wherein R is an organic moiety and may be alkyl, aryl, arylalkyl, alkylaryl or olefinic and X is a moiety containing at least one of halogen, oxygen, sulfur and nitrogen. Compounds denominated by the formula "R—X" include alcohols, ethers, mercaptans, sulfides, halides, carbonyl compounds (aldehydes and ketones), amines, alkanolamines and the like. The compound R—X is of an effective size such that R—X may enter the pore structure of the aluminophosphate whereby light olefin products are formed. The feedstock preferably comprises at least one aliphatic alcohol and/or ether derivatives thereof, more preferably at least one of methanol, ethanol, dimethyl ether and diethyl ether. The feedstock is converted to a hydrocarbon product and preferably contains a major amount of light olefinic products, i.e., $C_2$, $C_3$ and/or $C_4$ olefins based on the hydrocarbon products formed. The feedstock is contacted with a catalyst comprising an aluminophosphate molecular sieve as disclosed in U.S. Pat. No. 4,310,440 at effective process conditions to produce light olefins.

DETAILED DESCRIPTION OF THE INVENTION

The instant process relates to the conversion of compounds of the formula R—X to hydrocarbon products, preferably light olefins containing 2 to 4 carbon atoms, wherein said process comprises contacting a feedstock comprising at least one compound of the formula R—X, where R is an organic moiety and X is a moiety containing at least one of halogen, oxygen, sulfur and nitrogen. Compounds denominated by the formula "R—X" include alcohols, ethers, mercaptans, sulfides, halides, carbonyl compounds (aldehydes and ketones), amines, alkanolamines and the like. "R—X" is preferably an aliphatic alcohol or ether derivative thereof, more preferably at least one of methanol, ethanol, dimethyl ether and diethyl ether, with at least one aluminophosphate molecular sieve, defined herein as the aluminophosphates disclosed in U.S. Pat. No. 4,310,440, at effective process conditions to produce light olefin products. It should be noted that the [$AlO_2$] tetrahedral unit has a net negative charge and the [$PO_2$] tetrahedral unit has a net positive charge, although such are not designated herein as such.

The term "light olefins" is employed herein to refer to olefins having two to four carbon atoms, inclusive. Although other hydrocarbon products may be formed, products of particular interest herein are light olefins and the process is preferably carried out such that light olefin products are produced as the major hydrocarbon products i.e., over 50 mole percent of the hydrocarbon product is preferably light olefins. The ability of the aluminophosphate molecular sieves to catalytically convert compounds of the R—X type and, further, provide for the formation of light olefins, preferably as the major portion of the hydrocarbon product, has not heretofore been reported or suggested and, further, is surprising in view of the relatively low acidity of such aluminophosphate molecular sieves.

The aluminophosphates of U.S. Pat. No. 4,310,440 are described as having a framework structure whose chemical composition expressed in terms of mole ratios of oxides is:

$$Al_2O_3 : 1.0 \pm 0.2 P_2O_5$$

each of said framework structures being microporous in which the pores are uniform and have nominal diameters within the range of about 3 to about 10 Angstroms, an intracrystalline adsorption capacity for water at 4.6 torr and 24° C. of at least 3.5 weight percent, the adsorption and desorption of water being completely reversible while retaining the same essential framework topology in both the hydrated and dehydrated states. The aluminophosphate species of U.S. Pat. No. 4,310,440 are denominated as "$AlPO_4$-n" wherein "n" is a number specific to each individual member and include but are not limited to $AlPO_4$-5, $AlPO_4$-8, $AlPO_4$-9, $AlPO_4$-11, $AlPO_4$-12, $AlPO_4$-14, $AlPO_4$-16, $AlPO_4$-17, $AlPO_4$-18, $AlPO_4$-20, $AlPO_4$-21, $AlPO_4$-22, $AlPO_4$-23, $AlPO_4$-25, $AlPO_4$-26, $AlPO_4$-28 and $AlPO_4$-31. This designation is an arbitrary one and is not intended to denote structure or relationship to another material(s) which may also be characterized by a numbering system. Another member of this family is $AlPO_4$-33, which is disclosed in copending U.S. Ser. No. 480,698, filed Mar. 31, 1983, incorporated herein by reference thereto.

It has been discovered that aluminophosphate molecular sieves may be employed as catalyst(s) for the conversion of a "R—X" feedstock, preferably a feedstock comprising aliphatic alcohols and ether derivatives thereof. The conversion of such feedstocks to light olefin products may be obtained under process conditions similar to those disclosed heretofore in the prior art for aluminosilicate zeolite catalysts. By the use of specific aluminophosphate molecular sieves it is believed that the selectivity to $C_2$ to $C_4$ olefin products (i.e., ethylene, propylene, and butenes) will be at least about 25 molar percent, based on the total hydrocarbon products formed containing two carbons or more, preferably in excess of 50 mole percent and more preferably in excess of 75 mole percent. Further, high molar conversions i.e., preferably at least about 50 percent and most preferably at least about 90 percent, based on the moles of feedstock to products, are believed obtainable while forming a low molar amount of methane (preferably less than about ten (10) molar percent and more preferably less than about five (5) molar percent) and while forming only minor amounts of saturated hydrocarbons and $C_5$ and higher hydrocarbons (typically less than about 10 molar percent). Aromatic hydrocarbons may be below that which is detectable by standard vapor phase chromatographic techniques.

The feedstock employed herein is referred to as an "R—X" feedstock to denominate a feedstock comprising compounds of the formula "R—X" wherein "R" is an organic moiety including alkyl, alkenyl, aryl, alylalkyl, alkylaryl and mixtures thereof and "X" is a moiety containing at least one of halogen, oxygen, sulfur and nitrogen. Representative of the moiety "X" are halogen, hydroxyl, alkoxy, carbonyl (aldehyde and ketone groups), sulfide, amino, amide, mercapto, and the like. The compound R—X is preferably selected with consideration being given to the pore size of the aluminophosphate. The compound R—X is preferably selected by correlating such to the pore size of the aluminophosphate such that R—X may access the pore structure of the aluminophosphate whereby light olefin products are formed. It is recognized that external surface effects may result in the formation of some light olefin products as a result of the contact of R—X and the external surface of the aluminophosphate thereof. Preferred compounds having the general formula R—X include alcohols, ethers, mercaptans, sulfides, halides, carbonyl compounds (e.g., aldehydes and ketones), amides and amines. "R" is preferably an aliphatic moiety having from 1 to 10 carbon atoms and preferably contains between 1 and about 4 carbon atoms. Suitable reactants of the formula "R—X" are lower aliphatic alcohols, such as lower straight chain alkanols such as methanol, ethanol, normal propanol, butanols, pentanols, hexanols, heptanols, octanols, their unsaturated counterparts and mixtures thereof. The nitrogen, halogen and sulfur analogues of the aforementioned compounds may be employed, including methyl mercaptan, methyl amine, ethyl mercaptan, methyl amine, cyclohexylamine, n-propyl amine, methyl sulfide, methyl chloride, dimethyl ether, diethylether, methylethyl ether, formaldehyde, dimethyl ketone and mixtures of such with alcohols as above described.

The process is preferably carried out in the vapor phase such that the R—X feedstock is contacted in a vapor phase in a reaction zone with an aluminophosphate molecular sieve at effective process conditions to produce light olefins. The term "effective process conditions" includes an effective temperature, pressure, WHSV (Weight Hourly Space Velocity) and, optionally, an effective amount of diluent, wherein such are preferably correlated to produce light olefin products as the major hydrocarbon products. Alternatively, the process may be carried out in the liquid phase. When the process is carried out in the liquid phase the process necessarily involves the separation of products formed in a liquid reaction media and can result in different conversions and selectivities of the feedstock to products with respect to the relative ratios of the light olefin products as compared to that formed by a vapor phase process.

The temperature which may be employed in the process may vary over a wide range depending, at least in part, on the selected aluminophosphate catalyst. In general, the process can be conducted at an effective temperature between about 200° C. and about 700° C., preferably between about 250° C. and about 600° C., and most preferably between about 300° C. and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products if such are desired as the major products. Notwithstanding these factors, the reaction will still occur and the feedstock, at least in part, can be converted to the preferred light olefin products at temperatures outside the range between about 200° C. and about 700° C.

The process is effectively carried out over a wide range of pressures including autogenous pressures. At pressures between about 0.001 atmospheres and about 1000 atmospheres, the formation of products will be effected, although the optimum amount of product will not necessarily form at all pressures. The preferred pressure is between about 0.01 atmospheres and about 100 atmospheres. The pressures referred to herein for the process are exclusive of the inert diluent, if any is present, and refer to the partial pressure of the feedstock as it relates to "R—X" compounds. Pressures outside the stated range are not excluded from the scope of this invention, although such do not fall within certain desirable embodiments of the invention. At the lower and upper end of the pressure range, and beyond, the selectivities, conversions and/or rates to the preferred light olefin products may not occur at the optimum, although light olefin products may be formed.

The process is carried out for an effective period of time sufficient to produce products and preferably light olefin products. In general, the residence time employed to produce the hydrocarbon products can vary from seconds to a number of hours. It will be readily appreciated by one skilled in the art that the residence time will be determined to a significant extent by the reaction temperature, the aluminophosphate molecular sieve selected, the WHSV, the phase (liquid or vapor) selected, and, perhaps, selected process design characteristics.

The process is effectively carried out over a wide range of WHSV for the feedstock and is generally between about 0.01 hr$^{-1}$ and about 100 hr$^{-1}$ and preferably between about 0.1 hr$^{-1}$ and about 40 hr$^{-1}$. Weight Hourly Space Velocities above 100 hr$^{-1}$ may be employed and are intended to be covered by the instant process, although such are not preferred.

The instant process is most preferably carried out under effective process conditions comprising a temperature between about 300° C. and about 500° C., a pressure between about 0.1 atmosphere (one atmosphere equals 14.7 psia) to about 100 atmospheres, utilizing a WHSV expressed in hr$^{-1}$ for each component of the feedstock having a value between about 0.1 and about 40. The temperature, pressure, and WHSV are each selected such that the effective process conditions, i.e., the effective temperature, pressure, and WHSV, are employed in conjunction, i.e. correlated, with the selected aluminophosphate molecular sieve and selected feedstock such that the desired products are produced and preferably such that light olefin products are produced.

In addition to the presence of "R—X" compounds in the feedstock, a diluent may be present in the feedstock in an amount between about 1 and about 99 molar percent, based on the total number of moles of all feed components fed to the reaction zone (or catalyst). Typical of the diluents which may be employed in the instant process are helium, argon, nitrogen, carbon monoxide, carbon dioxide, hydrogen, water(steam), paraffins, hydrocarbons (such as methane and the like), aromatics (such as benzene, toluene, xylenes and the like), mixtures thereof, and the like. The addition of a diluent to the feedstock prior to such being employed in the instant process is generally believed to be beneficial, although such is not required.

The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such aluminophosphate molecular sieves in series to provide for a desired product mixture. Owing to the nature of the process, it may be desirous to carry out the instant process by use of the aluminophosphate catalyst in a dynamic (e.g. fluidized or moving) bed system or any system of a variety of transport beds rather than in a fixed bed system. Such systems would readily provide for any regeneration (if required) of the aluminophosphate molecular sieve catalyst after a given period of time. If regeneration is required, the aluminophosphate molecular sieve catalyst can be continuously introduced as a moving bed to a regeneration zone where it can be regenerated, such as for example by removing carbonaceous materials by oxidation in an oxygen-containing atmosphere. In the preferred practice of the invention, the catalyst will be subject to a regeneration step by burning off carbonaceous deposits accumulated during reactions.

ALUMINOPHOSPHATES

The selection of the aluminophosphate molecular sieve catalysts for the instant process is preferably related, in part, to the desired product mixture sought to be obtained. In all instances the aluminophosphate will be an aluminophosphate as generally disclosed in U.S. Pat. No. 4,310,440 and copending U.S. Ser. No. 480,698. The selected aluminophosphate molecular sieve preferably has a kinetic pore diameter (average kinetic diameter in Angstroms, Å) such that the selectivity to light olefin products is at least 50 molar percent. Accordingly, at least a portion, preferably a major portion, of the pores have an average kinetic diameter characterized such that the adsorption capacity (as measured by the standard McBain-Bakr gravimetric adsorption method using given adsorbate molecules) shows adsorption of oxygen (average kinetic diameter of about 3.46Å) and negligible adsorption of isobutane (average kinetic diameter of about 5.0Å). More preferably the average kinetic diameter is characterized by adsorption of Xenon (average kinetic diameter of about 4.0Å) and negligible adsorption of isobutane and most preferably by adsorption of n-hexane (average kinetic diameter of about 4.3Å) and negligible adsorption of isobutane. Negligible adsorption of oxygen or xenon is adsorption of less than four percent by weight of the adsorbate based on the weight of the aluminophosphate and adsorption of oxygen or Xenon is adsorption of greater than or equal to four percent by weight of the adsorbate based on the weight of the aluminophosphate. Negligible adsorption of n-hexane or isobutane is adsorption of less than two percent by weight of the adsorbate based on the weight of the aluminophosphate and adsorption of n-hexane or isobutane is adsorption of greater than or equal to two percent by weight of the adsorbate based on the weight of the aluminophosphate.

The McBain-Bakr gravimetric method should be carried out with reference to the following pressure and temperature for a given adsorbate:

| Adsorbate | Pressure (Torr) | Temperature (°C.) |
|---|---|---|
| $O_2$ | about 100 | −183 |
| n-hexane | about 45 | 20° C. to 25° C. |
| Xenon | about 750 | 20° C. to 25° C. |
| isobutane | about 760 | 20° C. to 25° C. |

Although it is clear that factors other than just the kinetic pore size will affect the products formed, including any occlusion of the pores, the exact nature of such other factors or their exact effect on the products formed are not understood at present. It is believed that the kinetic diameter of the pores of the aluminophosphate molecular sieve is related to the products formed. Although a specific aluminophosphate may not have a kinetic pore diameter within the desired or preferred range the aluminophosphate may be modified by depositing or impregnating such with cations, anions, salts and/or compounds that occlude or otherwise result in the modification of a aluminophosphates having a large pore size to one having a kinetic pore diameter(s) within the desired or preferred range.

Techniques which may be employed to effect the diminution of the pore size of a aluminophosphate molecular sieve are generally known in the art. Such procedures generally involve the introduction to a pore of a pore size restricting material and may involve such procedures as (1) impregnating the aluminophosphate with a solution comprising a solvent or solubilizing agent for such a pore restricting material (one or more) in an amount sufficient to deposit the desired weight of such pore restricting material to the aluminophosphate such that the desired pore size is obtained and/or (2) exchanging the aluminophosphate, to the extent possible if any, with a solution containing the pore size restricting material. The impregnation or deposition of the pore restricting materials may be generally accomplished by heating the aluminophosphate at an elevated temperature to evaporate any liquid present to effect deposition or impregnation of the pore restricting material into the interior and/or onto the exterior surface of the aluminophosphate, or by the exchange of cations present in the aluminophosphate with cations that provide for the desired average kinetic pore size. Alternatively, the pore restricting material may be formed on the aluminophosphate from an emulsion or slurry containing the pore restricting material by heating the aluminophosphate as described above. Impregnation and exchange procedures are generally the preferred techniques because they utilize and introduce the pore restricting material more efficiently than other procedures such as coating procedures since a coating procedure is generally not able to effect substantial introduction of the pore restricting material onto the interior surfaces of the aluminophosphate. The preferred method of introduction of pore restricting materials will be an impregnation or deposition method owing to the low level of ion-exchangability of the instant aluminophosphates. In addition, coated materials are more generally susceptible to the loss of the pore restricting materials by abrasion.

Suitable pore restricting materials include alkali metal, alkaline earth metals, transition metals and the salts thereof including inorganic and organic salts such as: nitrates, halides, hydroxides, sulfates and carboxylates. Other pore restricting materials generally employed in the art for such are also believed to be employable herein.

In carrying out the instant process the aluminophosphate molecular sieves may be admixed (blended) or provided sequential to other materials which may provide some property which is beneficial under process conditions, such as improved temperature resistance or improved catalyst life by minimization of coking or which is simply inert under process conditions. Such materials may include synthetic or naturally occurring substances as well as inorganic materials such as clays, silicas, aluminas, crystalline aluminosilicate zeolites, metal oxides and mixtures thereof. In addition, the aluminophosphate molecular sieves may be formed with materials such as silica, alumina, silica-alumina, silica-magnesia, silico-zirconia, silica-thoria, silica-berylia, silica-titania, as well as ternary compositions, such as silica-alumina-thoria, silica-alumina-zirconia and clays present as binders. The relative proportions of the above materials and the aluminophosphate may vary widely with aluminophosphate content ranging between about 1 and about 99 percent by weight of the composite.

EXPERIMENTAL PROCEDURE

The production of hydrocarbons in the examples was carried out by mixing about 0.5 gram of a selected aluminophosphate with 2.5 grams of quartz chips (20–30 U.S. Standard mesh). The resulting mixture was then placed in a ¼ inch (outside diameter) No. 304 stainless steel tubular reactor having a wall thickness of 0.035 inch. The tubular reactor was immersed in a fluidized heated sand bath having electrical resistance heaters provided for maintaining the sand bath and the tubular reactor at the desired temperature. Thermocouples were provided for measurement of the reactor temperature.

A selected feedstock was introduced to the tubular reactor by means of a Model 100 Altex Metering Pump (from Altex Corporation, a subsidiary of the Beckmann Corporation) concurrently with a stream of diluent with nitrogen and water (steam) being employed as diluents (unless otherwise noted in the examples hereinafter). The pressure employed in the examples was the autogenous pressure (about one (1) to about two (2) atmospheres unless otherwise noted. The ratios of these components are reported as weight ratios. When nitrogen was employed as a diluent it was introduced at a flow rate of about 5 cubic centimeters per minute.

The effluent from the tubular reactor (the reaction products) was analyzed. The liquid component of the effluent was collected at room temperature and subsequently analyzed by vapor phase chromatography, whereas the gaseous component of the effluent was sampled and analyzed directly from the effluent stream by vapor phase chromatography.

The analyses of both the liquid and vapor components of the effluent from the tubular reactor were carried out by programmed temperature chromatography having a thermal conductivity detector with a programmed increase in the chromatographic column's temperature over the chromatographic analysis. The analysis of the liquid and vaporous components of the effluent, including the analysis of all standards was carried out using chromatographic techniques by use of the following chromatographic instruments:

| | Phase Analyzed | |
|---|---|---|
| | Liquid | Vapor |
| Chromatograph | Varian 3700 | Hewlett Packard |
| Column | 20 feet × ⅛ inch (O.D.) stainless steel | 11 feet × ⅛ inch (O.D.) stainless steel |
| Packing | 10% Carbowax Chrom T 60/80 mesh | Porapak R |

When a product was not detected (ND) or if only a trace amount was qualitatively detected such is reported as ND or Trace. Further, although it has been observed that the methane and carbon dioxide formed in the process at temperatures of about 400° C. and higher are primarily derived from contact of the feedstock with the walls of the reactor these values are included since they do affect the efficiency of the overall process although their formation may be minimized by changes in the reactor design. The following examples are provided to exemplify the invention and are not meant to be limiting in any way. The $ALPO_4$'s employed in the examples hereinafter were the calcined $ALPO_4$'s as described in the referred to preparative example.

Examples 1 and 2

In example 1 the aluminophosphate denominated in U.S. Pat. No. 4,310,440 as $AlPO_4$-17 was employed in the instant process for the conversion of a feedstock comprising methanol and water to light olefin products. The conversion to light olefin products was measured at two different times during the example. The products contained about 3.1 mole percent carbon dioxide and about 60 mole percent dimethyl ether as non-hydrocarbon products. The molar efficiency to given hydrocarbon products, exclusive of non-hydrocarbon products, was measured and are set forth in Table I.

In example 2 the aluminophosphate denominated in U.S. Pat. No. 4,310,440 as $AlPO_4$-14 was employed according to the procedure as above described for $AlPO_4$-17, except that the results were measured at one time interval instead of at two time intervals. The products contained about 8.3 mole percent carbon dioxide and 69 mole percent dimethyl ether as non-hydrocarbon products. The results of this example are reported according to efficiency of a given hydrocarbon product, exclusive of non-hydrocarbon products, and are set forth in Table II.

TABLE I[1,2]

| Ethylene | 20.8 | 24.6 |
|---|---|---|
| Ethane | 1.1 | 1.6 |
| Propylene | 27.6 | 27.0 |
| Propane | 0.7 | 0.7 |
| Butenes[3] | 20.8 | 14.1 |
| $C_5$'s | 10.9 | 9.5 |
| $C_6$'s | 3.5 | 2.7 |
| Methane | 14.4 | 19.9 |
| Hours on Stream | 1.8 | 3.3 |
| Methanol Conversion[4] | 53 | 49 |

[1]Temperature of 425° C. at the autogenous pressure.
[2]WHSV (Methanol) = 0.86
  WHSV ($H_2O$) = 2.01
[3]Approximate value due to observed interference by methanol during analysis.
[4]Percent by Weight.

TABLE II[1,2]

| | |
|---|---|
| Ethylene | 14.7 |
| Ethane | 1.7 |
| Propylene | 27.6 |
| Propane | Trace |
| Butenes[3] | 12.1 |
| $C_5$'s | 8.3 |
| $C_6$'s | Trace |
| Methane | 35.5 |
| Hours on Stream | 1.0 |
| Methanol Conversion[4] | 51 |

[1]Temperature of 425° C. at the autogenous pressure.
[2]WHSV (Methanol) = 0.83 hr$^{-1}$
WHSV (H$_2$O) = 1.95 hr$^{-1}$
[3]Approximate value due to observed interference by methanol during analysis.
[4]Percent by Weight.

What is claimed is:

1. The process of producing hydrocarbons comprising contacting a feedstock comprising an organic compound of the formula R—X, where R is an organic moiety and X is a moiety containing at least one of halogen, oxygen, sulfur and nitrogen, at conversion conditions with an aluminophosphate molecular sieve having a framework structure whose chemical composition expressed in terms of mole ratios of oxides is $$Al_2O_3 : 1.0 \pm 0.2\ P_2O_5$$

each of said framework structures being microporous in which the pores are uniform and have nominal diameters within the range of about 3 to about 10 Angstroms, an intracrystalline adsorption capacity for water at 4.6 torr and 24° C. of at least 3.5 weight percent, the adsorption and desorption of water being completely reversible while retaining the same essential framework topology in both the hydrated and dehydrated states.

2. The process of claim 1 wherein said aluminophosphate molecular sieve is selected from the class consisting of AlPO$_4$-5, AlPO$_4$-8, AlPO$_4$-9, AlPO$_4$-11, AlPO$_4$-12, AlPO$_4$-14, AlPO$_4$-16, AlPO$_4$-17, AlPO$_4$-18, AlPO$_4$-20, AlPO$_4$-21, AlPO$_4$-22, AlPO$_4$-23, AlPO$_4$-25, AlPO$_4$-26, AlPO$_4$-28, AlPO$_4$-31, and AlPO$_4$-33.

3. The process of claim 1 wherein "R—X" is selected from the class consisting of compounds wherein "R" is an aliphatic moiety having from 1 to 10 carbon atoms and "X" is selected such that R—X is selected from the group consisting of alcohols, ethers, mercaptans, sulfides, halides, aldehydes, ketones, amines, amides.

4. The process of claim 1 wherein the aluminophosphate is characterized by adsorption of oxygen and negligible adsorption of isobutane.

5. The process of claim 1 wherein the aluminophosphate is characterized by adsorption of Xenon and negligible adsorption of isobutane.

6. The process of claim 1 wherein the aluminophosphate is characterized by adsorption of n-hexane and negligible adsorption of isobutane.

7. The process of claim 1 wherein said hydrocarbon products are light olefin products containing 2 to 4 carbon atoms and "R—X" is at least one of methanol, ethanol, dimethyl ether and diethyl ether.

8. The process of claim 7 wherein light olefins constitute at least about 25 molar percent of the hydrocarbon products.

9. The process of claim 8 wherein light olefin products constitute in excess of 50 molar percent of the hydrocarbon products.

10. The process of claim 1 wherein said feedstock contains diluent.

11. The process of claim 10 wherein said diluent is water and comprises between about 1 and about 99 molar percent of said feedstock.

12. The process of claim 1 wherein the feedstock is contacted with said aluminophosphate at a temperature between about 200° and about 700° C.

13. The process of claim 12 wherein the feedstock is contacted with said aluminophosphate at a temperature between about 300° and about 500° C.

14. The process of claim 1 wherein the process is conducted at a pressure between about 0.1 atmosphere and about 1000 atmospheres.

15. The process of claim 14 wherein the process is conducted at a pressure between about 0.1 atmosphere and about 100 atmospheres.

16. The process of claim 1 wherein said process is carried out in the vapor phase.

17. The process of claim 1 wherein said process is carried out in the liquid phase.

18. The process of claim 1 wherein the WHSV is between about 0.01 hr$^{-1}$ and about 100 hr$^{-1}$.

19. The process of claim 18 wherein the WHSV is between about 0.1 hr$^{-1}$ and about 40 hr$^{-1}$.

20. The process of claim 7 wherein the feedstock comprises methanol.

21. The process of claim 7 wherein the feedstock comprises methanol and dimethyl ether.

22. The process of claim 7 wherein the feedstock comprises ethanol.

23. The process of claim 7 wherein the feedstock comprises ethanol and diethyl ether.

24. The process of claim 7 wherein the feedstock consists essentially of methanol, dimethyl ether and water.

25. The process of claim 7 wherein the feedstock consists essentially of methanol and water.

26. The process of claim 7 wherein the feedstock consists essentially of ethanol and water.

27. The process of claim 7 wherein the feedstock consists essentially of dimethyl ether and water.

28. The process of claim 10 wherein the diluent is nitrogen.

29. The process of claim 10 wherein the diluent is a paraffin.

30. The process of claim 10 wherein the diluent is helium.

31. The process of claim 10 wherein the diluent is an aromatic compound.

32. The process of claim 3 wherein said feedstock comprises aliphatic alcohols and ether derivatives thereof containing from 1 to 5 carbon atoms.

* * * * *